United States Patent [19]

Kaji

[11] Patent Number: 5,219,496
[45] Date of Patent: Jun. 15, 1993

[54] NON-LINEAR OPTICAL MATERIAL AND NON-LINEAR OPTICAL DEVICES

[75] Inventor: Makoto Kaji, Hitachi, Japan

[73] Assignee: Hitachi Chemical Company, Tokyo, Japan

[21] Appl. No.: 717,670

[22] Filed: Jun. 19, 1991

[30] Foreign Application Priority Data

Jun. 27, 1990 [JP] Japan .................. 2-168744

[51] Int. Cl.$^5$ .................. F21V 9/00; F21V 9/04; F21V 9/06; G02B 6/10
[52] U.S. Cl. .................. 252/582; 252/587; 252/589; 359/328
[58] Field of Search .................. 252/582, 587, 589; 359/328; 385/122

[56] References Cited

U.S. PATENT DOCUMENTS

| 4,162,162 | 7/1979 | Dueber | 96/115 P |
| 4,774,157 | 9/1988 | Manring | 430/14 |
| 4,923,780 | 5/1990 | Taylor, Jr. | 430/257 |

OTHER PUBLICATIONS

D. S. Chemla, J. Zyss "Non-linear Optical Properties of Organic Molecules and Crystals, vol. 2, appendix I"; 1987, Academic Press, London.

Chemical Abstract, vol. 100, No. No. 26, 1983, Columbus, Ohio, US; Abst. No. 210746G C. A. Byrne, E. J. Poziomek; "Fluorescence in Polymers:2-(diphenylacetyl)-1,3-indanedione-1-imine derivatives in polymer matrixes".

Bahner et al., J. Med Chem., vol. 12, (1969), pp. 721-722.

Primary Examiner—Robert L. Stoll
Assistant Examiner—Philip Tucker
Attorney, Agent, or Firm—Antonelli, Terry, Stout & Kraus

[57] ABSTRACT

A non-linear optical material made of a compound represented by the formula:

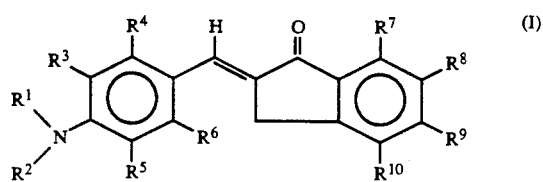

(I)

wherein $R^1$ and $R^2$ represent independently a hydrogen atom, an alkyl group having 1-22 carbon atoms, a hydroxyalkyl group having 1-22 carbon atoms, a haloalkyl group having 1-22 carbon atoms, a cyanoalkyl group having 1-22 carbon atoms or an aryl group having 6-10 carbon atoms; and $R^3$, $R^4$, $R^5$, $R^6$, $R^7$, $R^8$, $R^9$ and $R^{10}$ represent independently a hydrogen atom, an alkyl group having 1-10 carbon atoms, an alkoxyl group having 1-10 carbon atoms, a halogen atom, a cyano group, a hydroxyl group, an alkoxycarbonyl group having 2-22 carbon atoms, or an acyl group, has a high non-linear optical coefficient and is suitable for use in a non-linear optical device.

6 Claims, No Drawings

NON-LINEAR OPTICAL MATERIAL AND NON-LINEAR OPTICAL DEVICES

BACKGROUND OF THE INVENTION

This invention relates to novel non-linear optical material and non-linear optical devices which are essential for an optical signal processing system involving, for instance, such operations as optical parametric oscillation, harmonic generation and optical switching.

Non-linear optical material, which is expected to play an important role in the art of optical communication, is capable of performing multiple functions such as optical mixing, parametric oscillation, harmonic generation and optical switching owing to the non-linear optical response of the material. Hitherto, crystals of such inorganic substances as $KH_2PO_4$, $NH_4H_2PO_4$ and the like have been used as said non-linear optical material. These substances, however, are still unable to meet the requirements for said uses because of their low non-linear susceptibility, deliquescency and low damage threshold value.

Ever since clarification of excellent properties of organic non-linear optical materials making use of $\pi$ electron polarization by disclosure of the facts that said organic non-linear optical materials have a greater non-linear optical coefficient than the inorganic materials, have generally no deliquescency and are high in damage threshold value, the extensive studies and development have been made on organic non-linear optical materials in many fields of science. The results of the latest studies are given in detail in, for instance, D. S. Chemla and J. Zyss: Nonlinear Optical Properties of Organic Molecules and Crystals, Vols. 1 and 2, Academic Press, 1987.

Nevertheless, there is yet available no material having a large enough non-linear optical coefficient to enable attainment of the object with use of low-power laser such as semiconductor laser, and thus development of novel material capable of meeting said requirements has been strongly desired.

SUMMARY OF THE INVENTION

The present invention has for its object to provide novel organic non-linear optical material having a high non-linear optical coefficient and non-linear optical device using said material.

More specifically, the present invention provides non-linear optical material comprising a compound represented by the formula:

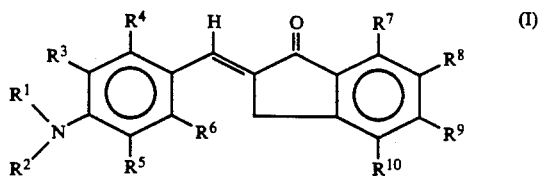

wherein $R^1$ and $R^2$ represent independently a hydrogen atom, an alkyl group having 1-22 carbon atoms, a hydroxyalkyl group having 1-22 carbon atoms, a haloalkyl group having 1-22 carbon atoms, a cyanoalkyl group having 1-22 carbon atoms or an aryl group having 6-10 carbon atoms; and $R^3$, $R^4$, $R^5$, $R^6$, $R^7$, $R^8$, $R^9$ and $R^{10}$ represent independently a hydrogen atom, an alkyl group having 1-10 carbon atoms, an alkoxyl group having 1-10 carbon atoms, a halogen atom, a cyano group, a hydroxyl group, an alkoxycarbonyl group having 2-22 carbon atoms or an acyl group, and the non-linear optical devices using said material.

DESCRIPTION OF THE PREFERRED EMBODIMENTS

The non-linear optical material provided according to the present invention is made of a compound represented by the following formula:

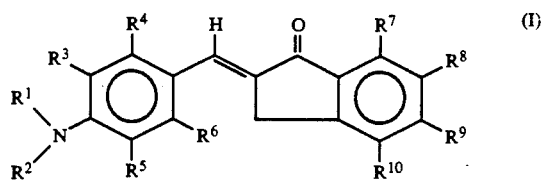

wherein $R^1$ and $R^2$ represent independently a hydrogen atom, an alkyl group having 1-22 carbon atoms, a hydroxyalkyl group having 1-22 carbon atoms, a haloalkyl group having 1-22 carbon atoms, a cyanoalkyl group having 1-22 carbon atoms or an aryl group having 6-10 carbon atoms; and $R^3$, $R^4$, $R^5$, $R^6$, $R^7$, $R^8$, $R^9$ and $R^{10}$ represent independently a hydrogen atom, an alkyl group having 1-10 carbon atoms, an alkoxyl group having 1-10 carbon atoms, a halogen atom, a cyano group, a hydroxyl group, an alkoxycarbonyl group having 2-22 carbon atoms or an acyl group.

In the present invention, there are used the aminobenzalindanone compounds represented by the above-shown formula (I). These aminobenzalindanone compounds can be routinely synthesized by subjecting 1-indanone and p-aminobenzaldehyde to aldol condensation according to, for example, the method described in detail in Organic Reaction, vol. 16.

Examples of the compounds represented by the formula (I) are 2-(4'-dimethylaminobenzal)-1-indanone, 2-(4'-diethylaminobenzal)-1-indanone, 2-(4'-di-n-butylaminobenzal)-1-indanone, 2-(4'-di-(2''-cyanoethyl)-aminobenzal)-1-indanone, 2-(4'-dimethylamino-2'-methylbenzal)-1-indanone, 2-(4'-diethylamino-2'-methylbenzal)-1-indanone, 2-(4'-dimethylamino-2'-methoxybenzal)-1-indanone, 2-(4-diethylamino-2'-methoxybenzal)-1-indanone, 2-(4'-dimethylamino-2'-ethylbenzal)-1-indanone, 2-(4'-diethylamino-2'-ethyl-benzal)1-indanone, 2-(4'-dimethylamino-2'-ethoxybenzal)1-indanone, 2-(4'-diethylamino-2'-ethoxybenzal)-1-indanone, and 2-[4-bis(2-chloroethyl)aminobenzal]indanone.

2-(4-diethylamino-2-methylbenzal)-1-indanone and 2-[4-bis(chloroethyl)aminobenzal]-1-indanone can be mentioned as preferred examples of said compounds for use in this invention.

For the preparation of the non-linear optical material of this invention, it is possible to use either a compound of the formula (I) or a composition prepared by dispersing or dissolving a compound of the formula (I) in a high-molecular compound.

As the high-molecular compound, there can be used, for example, homopolymers or copolymers of such monomers as methyl acrylate or methacrylate, ethyl acrylate or methacrylate, n-butyl acrylate or methacrylate, cyclohexyl acrylate or methacrylate, acrylic or methacrylic acid, styrene, vinyltoluene, divinylbenzene, vinyl chloride, $\beta$-hydroxyethyl acrylate or methacrylate and the like, polyesters, polyamides, polyurethanes, polycarbonates, cellulose esters, and polyethers. A compound of the formula (I) and a corresponding monomer may be mixed and dissolved, the mixture being then polymerized by the action of heat or light to form a composition. Also, a high-molecular compound such as mentioned above and a compound of the formula (I) may be dissolved and mixed by using a suitable solvent, followed by removal of the solvent to obtain a composition. It is possible to improve the non-linear optical performance by conducting poling in the course of the polymerization in the former case or after formation of the composition in either former or latter case.

The non-linear optical material according to this invention can be used independently in the form of bulk crystal or as a part of a waveguide type optical device such as fiber type, slab type, planar type or channel type optical device. Among the non-linear optical devices produced by using said non-linear optical material are the wavelength modulating devices making use of second harmonic generation, high frequency generation or optical parametric oscillation, phase modulating devices making use of electro-optical effect, and polarization plane modulating devices.

The compounds of this invention have in their structure a carbonyl group as acceptor group and a substituted or non-substituted amino group as donor group, and said acceptor group and donor group are separated by a conjugated benzene ring and double bond to provide a large dipole moment (especially a dipole moment of an excited state), so that a high non-linear susceptibility can be obtained. Also, these compounds have good crystalizing properties as the compound molecules are of high rigid owing to the presence of indanone ring.

The present invention will be described below more particularly with reference to Examples thereof.

Synthesis Examples of the aminobenzalindanone compounds are shown below.

SYNTHESIS EXAMPLE 1

Synthesis of 4-N,N-diethylamino-2-methylbenzaldehyde 45 g (586.6 mmol) of N,N-dimethylformamide and 91.9 g (586.6 mmol) of phosphorus oxychloride were placed in a 500 ml four-necked flask, and then a mechanical stirrer, a thermometer, a dropping funnel and a reflux condenser were set to the flask. Since heat generation begins upon mixing of the two reagents, the mixture was stirred well while cooling with water. Then, with the reaction system kept at a temperature below 30° C., 95.6 g (586.6 mmol) of N,N-diethyl-m-toluidine was added dropwise over a period of about one hour, after which stirring was further continued for 2 hours. The resulting reaction mixture was poured into ice-cold water and neutralized with 10N sodium hydroxide. The organic matter was extracted with ether, and after drying the extract, the ether was distilled away. The residue was distilled under reduced pressure to obtain the objective compound. Yield: 82 g (429.3 mmol, 73%), boiling point: 175°–181° C. (at 4 mmHg).

The structure of the product was confirmed by $H^1$-NMR spectrum.

δ (CDCl$_3$) 1.20 (N-ethyl, 6H, t, J=6.9 Hz), 2.61 (Ar-methyl, 3H, S), 3.42 (N-ethyl, 4H, q, J=6.9 Hz), 6.37 (Ar-H, 1H, d, J=2.0 Hz), 6.52 (Ar-H, 1H, dd, J=8.4 Hz, 2.0 Hz), 7.62 (Ar-H, 1H, d, J=8.4 Hz), 9.91 (CHO, 1H, S).

SYNTHESIS EXAMPLE 2

Synthesis of 2-(4'-N,N-diethylamino-2'-methylbenzal)-1-indanone 5 g (26.15 mmol) of 4-N,N-diethylamino-2-methylbenzaldehyde and 3.45 g (26.15 mmol) of 1-indanone were put into a 200 ml pear shaped flask. Then 50 ml of methanol having dissolved therein 0.5 g of sodium hydroxide was added and the mixture was refluxed under heating for about one hour with a reflux condenser while stirring the mixture with a magnetic stirrer. The refluxed solution was allowed to cool by itself and the produced yellow precipitate was filtered out, washed well with methanol and dried to obtain a crude product. A methylene chloride solution of said crude product was prepared and about 80 g of neutral alumina powder was suspended in the solution. The suspension was stirred well and the alumina adsorbent was filtered out. The filtrate was evaporated to remove methylene chloride and the crystals were precipitated from ethyl acetate. The precipitated crystals were filtered out and collected. Yield: 6.9 g (22.6 mmol, 86.4%). The structure of the product was determined by $H^1$-NMR spectrum using deuterated chloroform as solvent and tetramethylsilane as internal standard.

δ (CDCl$_3$) 1.21 (N-ethyl, 6H, t, J=7.0 Hz), 2.51 (Ar-methyl, 3H, S), 3.41 (N-ethyl, 4H, q, J=7.0 Hz), 3.98 (ethylene, 2H, d, J=2.2 Hz), 6.53 (Ar-H, 1H, d, J =2.45 Hz), 6.59 (Ar-H, 1H, dd, J=2.45, 8.85 Hz), 7.67 (Ar-H, 1H, d, J=8.85 Hz), 7.30–7.70 (Ar-H, 3H, m), 7.90 (Ar-H, 1H, d, J=7.6 Hz), 7.95 (vinyl, 1H, S).

λmax (MeOH): 207.1 nm, 277.8 nm, 452 nm.

The non-linear optical material of this invention is described below with reference to Examples thereof.

EXAMPLE 1

Second harmonic generation of 2-(4'-N,N-diethylamino-2'-methylbenzylidene)-1-indanone which was obtained according to the above-described synthesis process was examined by the powder method described in Journal of Applied Physics, Vol. 36, pp. 3798–3813, 1968. The specimen powder sieved to a particle size range of 50–150 μm was held between two plates of non-fluorescent slide glass (mfd. by Matsunami Glass Co., Ltd.) and irradiated with infra-red laser light by using Pulse Nd:YAG Laser SL-303 (mfd. by Spectrolaser System Inc., output: 850 mJ; half-width: 15 ns; output per pulse: 50 MW; beam diameter: 9.5 mm; wavelength: 1064 μm; repeating frequency: 10 Hz). The intensity of the generated second harmonics with a wavelength of 532 nm was measured by a photomultiplier through an IR filter and a UV filter. It was 17.5 times the intensity obtained with urea used as control.

EXAMPLE 2

The efficiency of second harmonic generation of 2-[4-bis(2-chloroethyl)aminobenzal]-1-indanone synthesized according to the method of above-described Synthesis Example 2 by using commercially available 4-bis(2-chloroethyl)aminobenzaldehyde was examined in the same way as Example 1. It was confirmed that the second harmonic generation efficiency by said compound was 8 times that by urea.

As apparent from the above results, it is possible to obtain an optical element having high non-linear optical performance by using the non-linear optical material of this invention.

What is claimed is:

1. A non-linear optical device using a non-linear optical material made of a compound represented by the formula:

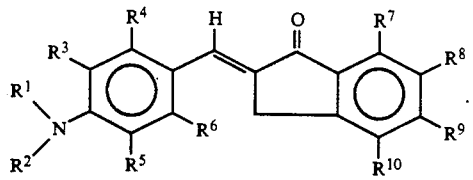

wherein $R^1$ and $R^2$ represent independently a hydrogen atom, an alkyl group having 1-22 carbon atoms, a hydroxyalkyl group having 1-22 carbon atoms, a haloalkyl group having 1-22 carbon atoms or an aryl group having 6-10 carbon atoms; and $R^3$, $R^4$, $R^5$, $R^6$, $R^7$, $R^8$, $R^9$ and $R^{10}$ represent independently a hydrogen atom or an alkyl group having 1-10 carbon atoms.

2. A non-linear optical device using a non-linear optical material made of a composition containing a compound represented by the formula:

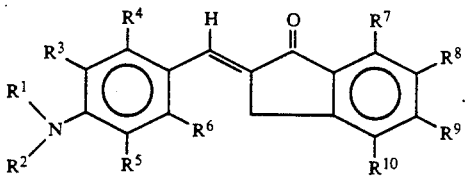

wherein $R^1$ and $R^2$ represent independently a hydrogen atom, an alkyl group having 1-22 carbon atoms, a hydroxyalkyl group having 1-22 carbon atoms, a haloalkyl group having 1-22 carbon atoms or an aryl group having 6-10 carbon atoms; and $R^3$, $R^4$, $R^5$, $R^6$, $R^7$, $R^8$, $R^9$ and $R^{10}$ represent independently a hydrogen atom or an alkyl group having 1-10 carbon atoms.

3. A non-linear optical device using a non-linear optical material made of an aminobenzalindanone compound represented by the formula:

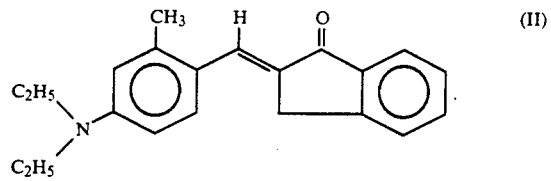

4. A non-linear optical device using a non-linear optical material made of a composition containing an aminobenzalindanone compound represented by the formula:

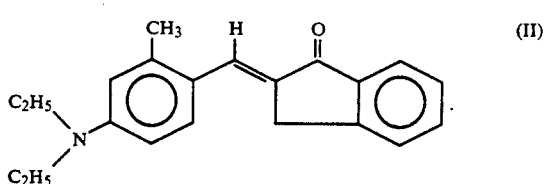

5. A non-linear optical device using a non-linear optical material made of an aminobenzalindanone compound represented by the formula:

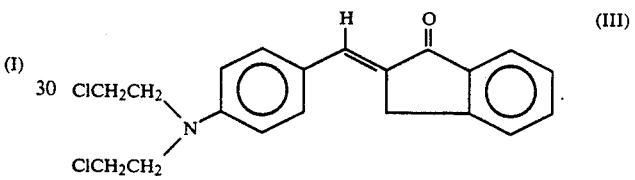

6. A non-linear optical device using a non-linear optical material made of a composition containing an aminobenzalindanone compound represented by the formula:

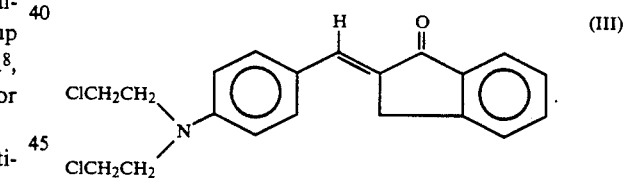

* * * * *